United States Patent
Akashi et al.

(10) Patent No.: US 10,073,085 B2
(45) Date of Patent: Sep. 11, 2018

(54) METHOD FOR PRODUCING ARTIFICIAL SKIN MODEL, AND ARTIFICIAL SKIN MODEL

(75) Inventors: Mitsuru Akashi, Suita (JP); Michiya Matsusaki, Toyonaka (JP); Takeshi Sakura, Kobe (JP); Koji Hashimoto, Toon (JP); Yuji Shirakata, Toon (JP); Satoshi Hirakawa, Hamamatsu (JP)

(73) Assignees: Osaka University, Osaka (JP); Toray Industries, Inc., Tokyo (JP)

( * ) Notice: Subject to any disclaimer, the term of this patent is extended or adjusted under 35 U.S.C. 154(b) by 0 days.

(21) Appl. No.: 14/008,348

(22) PCT Filed: Mar. 29, 2012

(86) PCT No.: PCT/JP2012/058329
§ 371 (c)(1),
(2), (4) Date: Sep. 27, 2013

(87) PCT Pub. No.: WO2012/133629
PCT Pub. Date: Oct. 4, 2012

(65) Prior Publication Data
US 2014/0024010 A1   Jan. 23, 2014

(30) Foreign Application Priority Data
Mar. 29, 2011   (JP) .................. 2011-072207

(51) Int. Cl.
*G01N 33/50*   (2006.01)
*C12N 5/071*   (2010.01)

(52) U.S. Cl.
CPC ....... *G01N 33/5088* (2013.01); *C12N 5/0698* (2013.01); *C12N 2502/094* (2013.01); *C12N 2502/1192* (2013.01); *C12N 2502/1323* (2013.01); *C12N 2502/28* (2013.01); *C12N 2503/06* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| RE35,399 E * | 12/1996 | Eisenberg ............... | A61F 2/105 128/DIG. 8 |
| 5,654,135 A | 8/1997 | Tinois et al. | |
| 5,667,961 A | 9/1997 | Bernard et al. | |
| 2004/0009591 A1 * | 1/2004 | Comer et al. ........... | 435/366 |
| 2004/0096816 A1 | 5/2004 | Perrier et al. | |
| 2007/0207540 A1 | 9/2007 | Akashi et al. | |
| 2008/0039940 A1 | 2/2008 | Hashimoto et al. | |
| 2011/0086068 A1 | 4/2011 | Gourdie et al. | |
| 2011/0217726 A1 | 9/2011 | Matsusaki et al. | |
| 2011/0281351 A1 | 11/2011 | Adachi et al. | |
| 2012/0210451 A1 | 8/2012 | Shimizu et al. | |
| 2014/0024010 A1 | 1/2014 | Akashi et al. | |
| 2015/0250925 A1 | 9/2015 | Akashi et al. | |

FOREIGN PATENT DOCUMENTS

| DE | 102006006461 | 8/2007 |
|---|---|---|
| JP | 2773058 B | 4/1998 |
| JP | 2004-166685 | 6/2004 |
| JP | 2005-269923 | 10/2005 |
| JP | 2010-172247 | 8/2010 |
| JP | 2011-004935 | 1/2011 |
| JP | 2012-115254 | 6/2012 |
| JP | 2012-205516 | 10/2012 |
| WO | WO 2005/087286 | 9/2005 |
| WO | 2007/090575 | 8/2007 |
| WO | WO 2009/118283 | 10/2009 |
| WO | 2010/055829 | 5/2010 |
| WO | 2010/087397 | 8/2010 |
| WO | 2011/016423 | 2/2011 |
| WO | 2012/133629 | 10/2012 |

OTHER PUBLICATIONS

Dzamba et al., Journal of Cell Science, vol. 100, pp. 605-612 (1991).*
Danhier et al., Targeting of tumor endothelium by RGD-grafted PLGA-nanoparticles loaded with Paclitaxel, Journal of Controlled Release, 140 (2009), pp. 166-173.*
La Zerda et al., Carbon nanotubes as photoacoustic molecular imaging agents in living mice, Nature Nanotechology, vol. 3, 2008, pp. 557-562.*
Chetprayoon et al.: "Evaluation on Stability of Laminated Tissues Fabricated by Hierarchical Cell Manipulation Technique"; Polymer Preprints, Japan, 2010, vol. 59, No. 2, p. 4837, with fill translation (5 pages).
Kadowaki et al.: "Evaluation on Specific Production of Heat Shock Protein from Laminated Tissues Constructed by Hierarchical Cell Manipulation Technique"; the 32$^{nd}$ Annual Meeting of the Japanese Society for Biomaterials, Nov. 29, 2010, with full translation (5 pages).
Matsusaki et al.: Construction of Laminated Tissue Model by Nanofilm Fabrication Technique; Brain 21, 2008, vol. 11, No. 4, pp. 94-100, with partial translation (17 pages).

(Continued)

*Primary Examiner* — Renee Claytor
*Assistant Examiner* — Evelyn Y Pyla
(74) *Attorney, Agent, or Firm* — Hamre, Schumann, Mueller & Larson, P.C.

(57) ABSTRACT

Provided is a novel method capable of producing an artificial skin model. A method for producing an artificial skin model includes: providing coated cells (1), each of which is obtained by covering the surface of a cell (3) with a coating film (2) containing an extracellular matrix component; forming a dermis tissue layer (7), in which the coated cells (1) are laminated, by culturing the coated cells (1); and forming an epidermis layer (12) by arranging epidermis cells (8) on the dermis tissue layer (7).

8 Claims, 7 Drawing Sheets

(56) References Cited

OTHER PUBLICATIONS

Matsusaki: "Development of Hierarchical Cell Manipulation Technique Capable of Constructing a Tailor-made Three-dimensional Complex Tissue in Vitro"; New Energy and Industrial Technology Development Organization, Graduate School of Engineering, Osaka University, Jul. 2009, http://www.nedo.go.ip/content/100082624.pdf, with full translation (6 pages).

Matsusaki: "Three-dimensional Organization of Cells by Nanostructured Biodegradable Polymeric Nanofilms", The Mazda Foundation Research Report, Graduate School of Engineering, Osaka University, 2008, vol. 20, pp. 55-61, with partial translation (17 pages).

Bell et al.: "Living Tissue Formed in vitro and Accepted as Skin-Equivalent Tissue of Full Thickness"; Science, vol. 211, 1981, pp. 1052-1054.

Maruguchi et al.: "Cultured Artificial Skin Containing Keratinocytes and Fibroblasts"; Journal of Japan Society of Plastic and Reconstructive Surgery, vol. 12, 1992, pp. 351-358.

Tsukahara et al.: "The Behavior of Macrophages in the Wound Healing Process in Human Skin Using a New Artificial Skin Model with Macrophages"; Journal of the Medical Association (Showa Igakukai), vol. 70, No. 2, 2010, pp. 164-173.

Gibot et al.: "Development of a human endothelialized reconstructed skin by tissue engineering to study melanoma biology"; Journal of Investigative Dermatology (2009), vol. 129, Suppl. 1, p. S138.

Gibot et al.: "A preexisting Microvascular Network Benefits in Vivo Revascularization of a Microvascularized Tissue-Engineered Skin Substitute"; Tissue Engineering: Part A, vol. 16, No. 10, 2010, pp. 3199-3206.

Suzuki: "Tissue engineering of skin—artificial skin, cultured skin"; BIO Clinica, vol. 15, No. 14, 2000 (1109), pp. 35-39.

Yoshizato; "Cell differentiation and proliferation in collagen gels—three-dimensional collagen gel culture as a model for studying tissue and organ formation"; Experimental Medicine, vol. 11, No. 2, 1993, pp. 27-32.

Yannas et al.: "Synthesis and characterization of a model extracellular matrix that induces partial regeneration of adult mammalian skin"; Proc. Natl. Acad. Sci, USA, vol. 86, Feb. 1989, pp. 933-937.

Suzuki et al.: "Regeneration of skin tissue and bFGF slow-release"; Gene & Medicine, vol. 6, No. 3 (2002), pp. 68-71.

Yang et al.: "New skin-equivalent model from de-epithelialized amnion membrane"; Cell Tissue Res. (2006) 326, pp. 69-77.

Fujimoto et al.: "Fabrication of Human Skin Equivalents by Hierarchical Cell Manipulation Technique"; 60th SPSJ Annual Meeting, May 11, 2011.

Nishiguchi et al.: "Rapid Construction of Heterocellular 3D-Tissues by Cell-accumulation Technique Using Layer-by-layer Nanofilms onto Cell Surface"; 60th SPSJ Annual Meeting, May 11, 2011.

Nishiguchi et al.: "Control of Cellular Functions by Preparation of Layer-by-layer Nanofilms onto the Cell Surface"; 59th SPSJ Annual Meeting, May 11, 2010.

Matsusaki, et al., "Kekkan Oyobi Limph-kan'yo Network o Yusaru Hifu Model no Kochiku", Regenerative Medicine, vol. 11, Supl 2012, p. 164, O-04-01, May 15, 2012—The contents of this document are included in NPL4 cited below.

Uchino, et al., "Constrution of Three-dimensional Human Skin Model Involving Dendritic Cells and its Application to Skin Sensitization Test", Journal of the Pharmaceutical Society of Japan, vol. 128, No. 1, pp. 45-50, 2008—Abstract.

Lammers, et al., "A molecularly defined array based on native fibrillar collagen for the assessment of skin tissue engineering biomaterials", Biomaterials, vol. 30, pp. 6213-6220, 2009.

Matsusaki, et al., "Development of Human Skin Equivalents Containing Reconstructed Blood and Lymph Capillaries", Eio Ind., vol. 29, No. 1, pp. 46-51, 2011—Full English Translation.

Uchino, et al., "Construction of a Three-Dimensional Human Skin Model Consisting of Keratinocytes, Dendritic Cells and Fibroblasts and Application of this Model for Alternative Animal Testing of Immune-Sensitizing Compounds", J. Soc. Cosmet. Chem. Jpn., vol. 41, No. 4, pp. 246-253, 2007.

Uchino, et al., "Construction of three-dimensional human skin model involving dendritic cells and its application to skin sensitization test", The Pharmaceutical Society of Japan—Proceedings of Annual Meeting, vol. 127, No. 1, p. 259, 2007—The contents of this document are included in NPL2 cited above.

Fujimoto, et al., "Fabrication of Layer-by-Layer Nanofilms Composed of Basal Lamina Components of Human Skin Equivalents" Polymer Preprints, The Society of Polymer Science Proceedings (CD-ROM), vol. 61, No. 1, p. 3H13, May 2012—Abstract.

Laubach, et al., "Integration of Langerhans-like cells into human skin equivalent", Arch Dermatol Res., vol. 303, pp. 135-139, 2011.

Fujimoto, et al., "Development of Human Skin Equivalents Involving Dendritic Cells by Cell Accumulation Technique and their Application for Immunological Responses", 2 pages—Abstract.

Nishiguchi, et al., "Rapid Construction of Three-Dimensional Multilayered Tissues with Endothelial Tube Networks by the Cell-Accumulation Technique", Adv. Mater., vol. 23, pp. 3506-3510, 2011.

Bechetoille, et al., Effects of solar ultraviolet radiation on engineered human skin equivalent containing both Langerhans cells and dermal dendritic cells, tissue Engineering, 13(11), 2267-2269, specif. pp. 2668,2670, 2007.

Uchino, et al, "Reconstruction of three-dimensional human skin model composed of dendritic cells, keratinocytes and fibroblasts utilizing a handy scaffold of collagen vitrigel membrane" Toxicology in Vitro 23: 333-337, specif. pp. 333, 334, 2009.

English Machine Translation—Matsusaki, et al., "Method and Kit for Detecting Biological Signal of Three-Dimensional Cell Culture Material", International Publication No. (JP)WO 2010/055829 A1, Apr. 12, 2012.

Dezutter-Dambuyant, et al., "Evolutive skin reconstructions: From the dermal collagen-glycosaminoglycan-chitosane substrate to an immunocompetent reconstructed skin", Bio-Medical Materials and Engineering 16 (2006), S85-S94, Specif. pp. S85, S86, S89 & S90.

Black, et al., "Optimization and Characterization of an Engineered Human Skin Equivalent", Tissue Engineering, vol. 11, No. 5/6, 2005, pp. 723-733, specif. p. 723.

English Machine Translation—Dietmar, et al., "Skin Model with Dendritic Cells", International Publication No. WO 2007/090575 A1, Aug. 16, 2007, specif. pp. 2, 6, 7 & 10.

Office Action issued in corresponding Japanese Patent Application No. 2014-534394, dated Apr. 19, 2018, 4 pages.

* cited by examiner

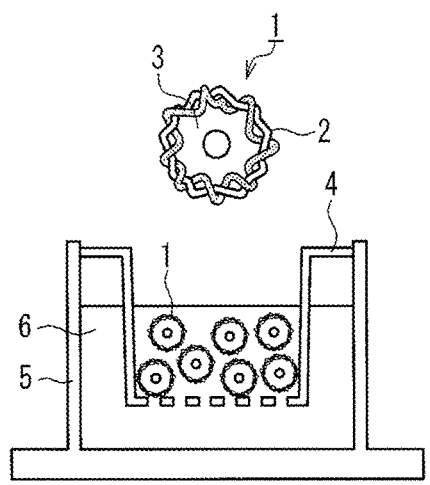
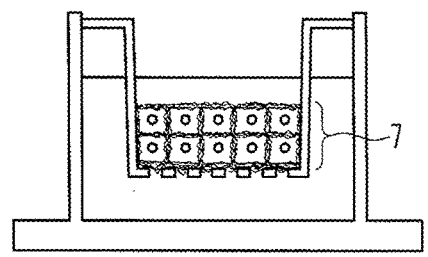
FIG. 1A  FIG. 1B
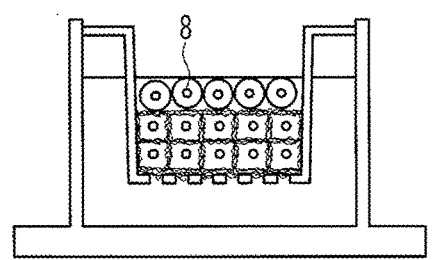
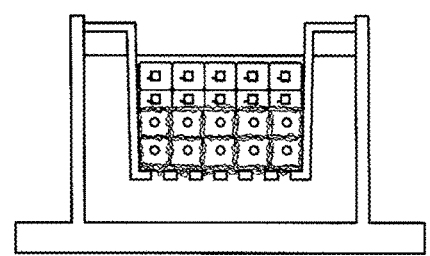
FIG. 1C  FIG. 1D
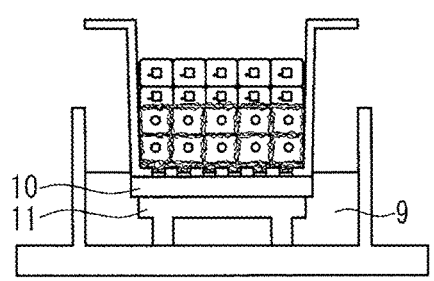
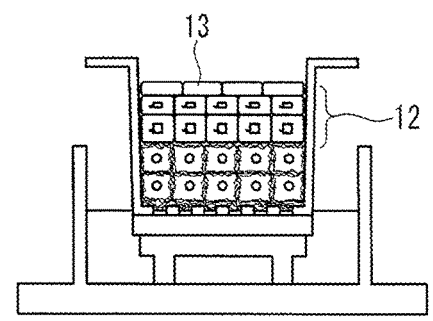
FIG. 1E  FIG. 1F

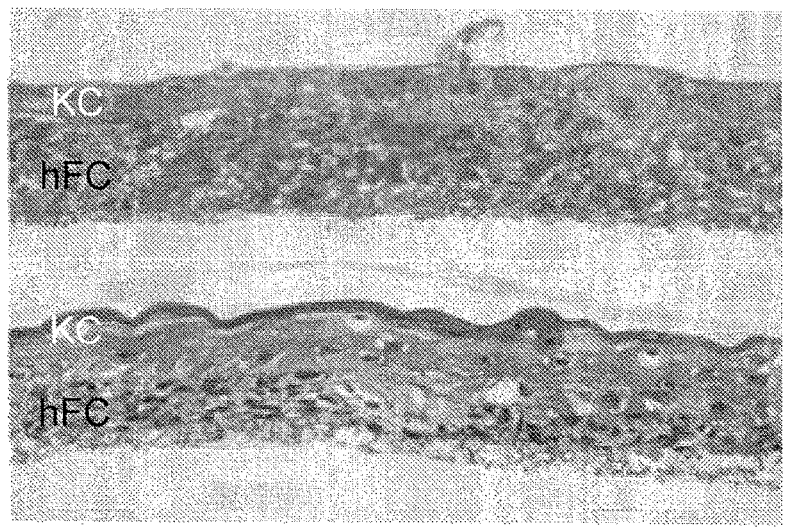
FIG. 4A
FIG. 4B
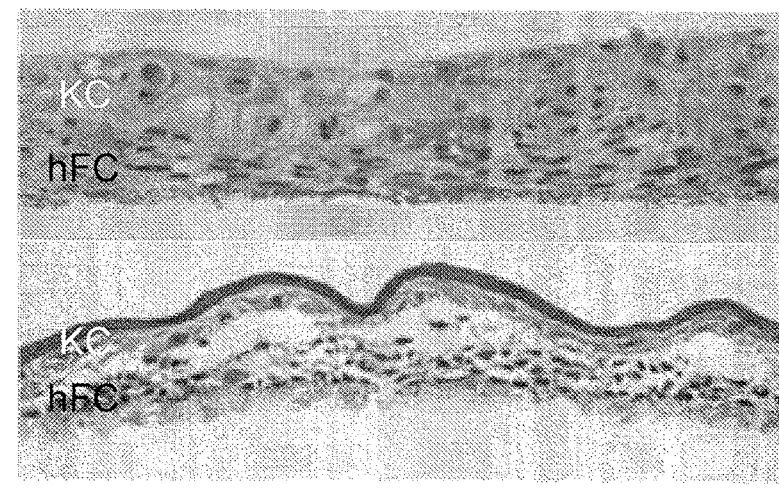
FIG. 5A
FIG. 5B
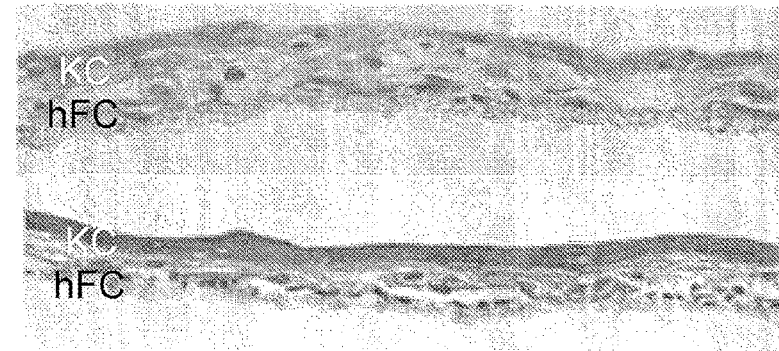
FIG. 6A
FIG. 6B

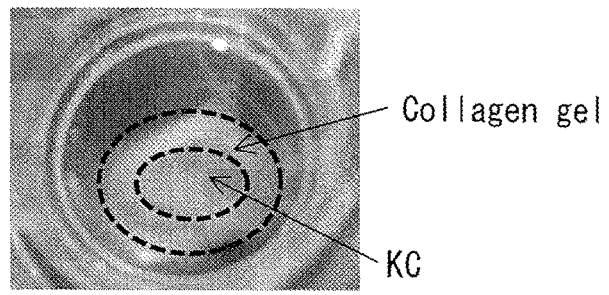
FIG. 7
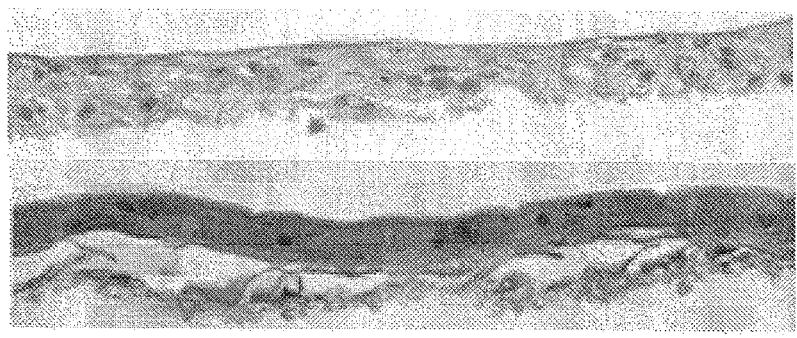
FIG. 8A
FIG. 8B

METHOD FOR PRODUCING ARTIFICIAL SKIN MODEL, AND ARTIFICIAL SKIN MODEL

TECHNICAL FIELD

The present invention relates to a method for producing an artificial skin model, and an artificial skin model produced by the method.

BACKGROUND ART

In research and development of substances to be directly applied to humans, such as cosmetic products, medicinal products, and nonmedicinal products, evaluation tests for substances such as a drug effect test, a pharmacological test, and a safety test are important. Conventionally, these tests have been conducted through use of animals such as mice and rats. However, in recent years, there is a demand for reconsidering an animal test from the viewpoint of animal protection, and various methods replacing the animal test have been proposed. As one of the methods, there is given an in vitro test or the like using a cultured skin model.

Further, in the fields of transplantation medicine and regeneration medicine, a cultured skin has been used as a covering material for treating a burn or a wound.

For the above-mentioned reasons, research and development of a cultured epidermis, a cultured skin, and the like have been extensively performed, and various proposals have been made. For example, there are a cultured epidermis obtained by culturing epidermis cells on collagen gel three-dimensionally (for example, Patent Document 1); and a cultured skin including a dermis and an epidermis obtained by arranging an amnion with an epithelium removed therefrom on collagen in which fibroblasts are embedded, and inducing the differentiation of normal human keratinized cells on the aminon to form an epidermis layer (for example, Patent Document 2 and Non-Patent Document 1, etc.). In addition, there is a method for producing a high-density dermis-like tissue through use of a reactor in which a mesh member and a liquid flow-controlling member are provided in a route for circularly culturing a cell culture liquid containing an extracellular matrix component and cells, and then, forming an epidermis layer through use of epidermis cells and a recombinant protein obtained by combining a cell growth factor and a collagen-bound domain (for example, Patent Document 3).

PRIOR ART DOCUMENTS

Patent Document

Patent Document 1: JP 2773058
Patent Document 2: WO2005/087286
Patent Document 3: JP 2010-172247 A

Non-Patent Document

Non-Patent Document: K. Hashimoto et al., Cell Tissue Res. 2006, 69, 326.

DISCLOSURE OF INVENTION

Problem to be Solved by the Invention

However, in the case where collagen gel is used as a support as in Patent Documents 1 and 2 and Non-Patent Document 1, the following problems arise along with the contraction and decomposition of the collagen gel: long-term stability is degraded; and the adhesiveness between an epidermis layer and a dermis layer becomes unstable. Further, the method of Patent Document 3 has a problem in that a special device is required for forming a dermis layer, and a problem in that a recombinant protein obtained by combining a cell growth factor and a collagen-bound domain is required for forming an epidermis layer. Therefore, there is a demand for a novel method capable of producing an artificial skin model.

The present invention provides a novel method capable of producing an artificial skin model.

Means for Solving Problem

The present invention relates to a method for producing an artificial skin model including: providing coated cells, each of which is obtained by covering a surface of a cell with a coating film containing an extracellular matrix component; forming a dermis tissue layer, in which the coated cells are laminated, by culturing the coated cells; and forming an epidermis layer by arranging epidermis cells on the dermis tissue layer.

Effects of the Invention

According to the present invention, for example, a novel method capable of producing an artificial skin model can be provided.

BRIEF DESCRIPTION OF DRAWINGS

FIG. 1 shows schematic views of an example of a method for producing an artificial skin model of the present invention.

FIG. 4A is an example of a photomicrograph before differentiation induction of an artificial skin model of Example 1, and FIG. 4B is an example of a photomicrograph of the artificial skin mode.

FIG. 5A is an example of a photomicrograph before differentiation induction of an artificial skin model of Example 2, and FIG. 5B is an example of a photomicrograph of the artificial skin model.

FIG. 6A is an example of a photomicrograph before differentiation induction of an artificial skin model of Example 3, and FIG. 6B is an example of a photomicrograph of the artificial skin model.

FIG. 7 is an example of a photomicrograph of a cultured skin of Comparative Example 1.

FIG. 8A is an example of a photomicrograph before differentiation induction of a cultured skin of Reference Example 1, and FIG. 8B is an example of a photomicrograph of the cultured skin.

DESCRIPTION OF THE INVENTION

Figure 2A:
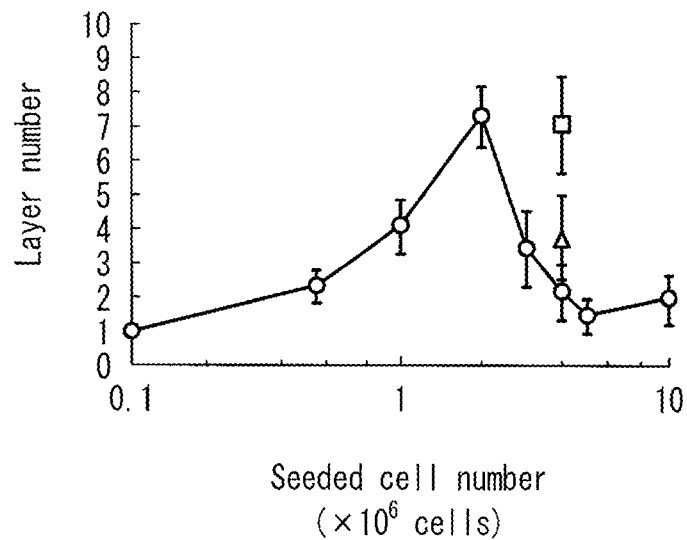
FIG. 2A is an example of a graph showing a relationship between the seeded cell number and the layer number of laminated cells.

The present invention is based on the following finding: if a dermis tissue layer is formed by culturing coated cells, each of which is obtained by covering the surface of a cell with a coating film containing an extracellular matrix component, and an epidermis layer is formed on the dermis tissue layer, an artificial skin model can be obtained, for example, even in the case where collagen gel serving as a support for laminating cells, a special device, a recombinant protein, or the like is not used. It should be noted that the present invention does not exclude using the special device and/or the recombinant protein obtained by combining a cell growth factor and a collagen-bound domain, and the special device and/or the recombinant protein may or may not be used in a production method of the present invention.

According to the production method of the present invention, coated cells are used for forming a dermis tissue layer, and hence, for example, a dermis tissue layer can be formed easily within a short period of time. Further, according to the production method of the present invention, coated cells are used for forming a dermis tissue layer, and hence a dermis tissue layer excellent in long-term stability of a laminated structure can be formed. Therefore, according to the production method of the present invention, an artificial skin model excellent in long-term stability can be produced easily within a short period of time. According to the production method of the present invention, an epidermis layer can be formed directly on a dermis tissue layer, and hence an artificial skin model excellent in adhesiveness between the dermis tissue layer and the epidermis layer can be produced.

According to the production method of the present invention, an artificial skin model including a dermis tissue layer and an epidermis layer, in which a transepithelial electric resistance (TER) can be measured, is produced. Therefore, according to the artificial skin model of the present invention, for example, the barrier function of a skin (epidermis layer) can be evaluated in a state closer to in vivo. Although a mechanism capable of measuring a TER in the artificial skin model produced by the production method of the present invention is not clear, the following can be presumed. That is, it is considered that, when the differentiation of epidermis cells is induced on a dermis tissue layer formed by culturing coated cells, the denseness in an epidermis layer is enhanced, adjacent epidermis cells contact each other, and a tight junction is formed between the epidermis cells. It should be noted that the present invention may not be interpreted to be limited to this mechanism.

That is, the present invention relates to the following.

[1] A production method for an artificial skin model, including: providing coated cells, each of which is obtained by covering a surface of a cell with a coating film containing an extracellular matrix component; forming a dermis tissue layer, in which the coated cells are laminated, by culturing the coated cells; and forming an epidermis layer by arranging epidermis cells on the dermis tissue layer.

[2] The production method described in [1], wherein the providing coated cells includes bringing the cell into contact with a first material having an RGD sequence and a second material that interacts with the first material alternately to form the coating film containing the extracellular matrix component on the surface of the cell, the coating film including a coating film containing the first material and a coating film containing the second material.

[3] The production method described in [2], wherein the first material is selected from the group consisting of fibronectin, vitronectin, laminin, cadherin, polylysine, elastin, collagen bound to an RGD sequence, gelatin bound to an RGD sequence, chitin, and chitosan, and the second material is selected from the group consisting of gelatin, dextran sulfate, heparin, hyaluronic acid, globulin, albumin, polyglutamic acid, collagen, and elastin.

[4] The production method described in any one of [1] to [3], including forming a tissue ancillary organ in the dermis tissue layer.

[5] The production method described in any one of [1] to [4], wherein the forming a dermis tissue layer includes: forming a cell layer, in which the coated cells are laminated, by culturing the coated cells; arranging cells forming the tissue ancillary organ on the cell layer; and forming a cell layer in which the coated cells are laminated by arranging the coated cells on the cell layer in which the cells forming the tissue ancillary organ are arranged and culturing the coated cells arranged on the cell layer.

[6] The production method described in any one of [1] to [5], wherein the forming a dermis tissue layer includes arranging the coated cells so that the coated cells are laminated in at least two layers.

[7] An artificial skin model produced by the production method described in any one of [1] to [6], including: a dermis tissue layer containing an extracellular matrix component and laminated cells; and an epidermis layer formed on the dermis tissue layer.

[8] The artificial skin model described in [7], wherein a tight junction is formed between adjacent epidermis cells in the epidermis layer.

[9] The artificial skin model described in [7] or [8], including a tissue ancillary organ formed in the dermis tissue layer.

[10] A method for evaluating irritation of a test substance with respect to a skin through use of the artificial skin model described in any one of [7] to [9], the method including: bringing the test substance into contact with the artificial skin model; and measuring a response of the artificial skin model to stimulation caused by the contact with the test substance.

[11] An evaluation kit for evaluating irritation of a test substance, including the artificial skin model described in any one of [7] to [9].

The term "artificial skin model" as used herein refers to a model reproducing or imitating the structure of a human skin, in particular, the structure of a portion including an epidermis and a dermis, and an environment thereof. Further, the artificial skin model preferably includes those which are to be experiment or test tools available for drug evaluation such as a drug effect test, a pharmacological test, and a safety test of a test substance with respect to a skin, and more preferably includes the artificial skin model produced by the production method of the present invention. The artificial skin model may include, for example, a tissue ancillary organ included in a skin and/or cells forming the tissue ancillary organ. Examples of the tissue ancillary organ include a blood vessel, a lymphatic vessel, an oil gland, a sweat gland, hair, and hair follicle. Examples of cells forming the tissue ancillary organ include vascular endothelial cells, lymphatic vessel endothelial cells, immunocytes, melanocytes, dendritic cells, Langerhans cells, follicular cells, hair papilla cells, sebaceous gland cells, and fat cells. Further, the artificial skin model may include cells other than the foregoing. Examples of the other cells include cancer cells, and cells which are present or can be present around cancer.

The term "coated cells" as used herein refers to cells each including a coating film containing an extracellular matrix component and a cell, in which the surface of the cell is covered with the coating film. Examples of the cells include adherent cells such as fibroblasts, epithelium cells, vascular endothelial cells, lymphatic vessel endothelial cells, neurons, tissue stem cells, embryo-stem cells, and immunocytes. One kind or two or more kinds of the cells may be used.

The term "dermis tissue layer" as used herein refers to a layer composed of an assembly of cells and an extracellular matrix component, in which coated cells are laminated three-dimensionally, and preferably refers to a layer similar to and/or imitating a form and/or an environment of a dermis of a skin. The dermis tissue layer may include the above-mentioned tissue ancillary organ and/or cells forming the tissue ancillary organ.

[Method for Producing an Artificial Skin Model]

The method for producing an artificial skin model of the present invention includes: providing coated cells, each of which is obtained by covering a surface of a cell with a coating film containing an extracellular matrix component; forming a dermis tissue layer, in which the coated cells are laminated, by culturing the coated cells; and forming an epidermis layer by arranging epidermis cells on the dermis tissue layer.

[Coated Cells]

The coated cells can be prepared by forming a coating film containing an extracellular matrix component on the surface of each cell. The term "extracellular matrix component" as used herein refers to a biological substance that fills a space outside cells in a living body and that performs functions such as a skeletal function, a function of providing a scaffold, and/or a function of holding a biological factor. Further, the extracellular matrix component may contain a substance that can perform functions such as a skeletal function, a function of providing a scaffold, and/or a function of holding a biological factor in in-vitro cell culture.

It is preferred that the coating film containing an extracellular matrix component include a film containing a material X and a film containing a material Y that interacts with the material X. Examples of the material X include a first material having an RGD sequence and a first material having positive charge. Examples of the material Y include a second material that interacts with the first material having an RGD sequence and a second material having negative charge. It is preferred that the coating film containing an extracellular matrix component include a film containing a first material having an RGD sequence (hereinafter, which may be also referred to as "first material") and a second material that interacts with the first material (hereinafter, which may be also referred to as "second material") from the viewpoint of ease of a formation operation, ease of thickness adjustment, and cell culture efficiency. It is more preferred that the above-mentioned films be laminated alternately from the viewpoint of enhancing the adhesiveness between adjacent coated cells. From the viewpoint of enhancing the adhesiveness between adjacent coated cells, it is preferred that the coating film containing an extracellular matrix component be a film formed adjacent to a cell surface and/or a film of an outermost layer; it is more preferred that at least the film of the outermost layer be a film containing the first material; and it is still more preferred that the film adjacent to the cell surface and the film of the outermost layer be films each containing the first material. The film containing the first material is preferably a film substantially made of the first material, and the film containing the second material is preferably a film substantially made of the second material.

(First Material Having an RGD Sequence)

The first material having an RGD sequence refers to a protein or a polymer having an "Arg-Gly-Asp" (RGD) sequence that is an amino acid sequence having cell adhesion activity. The term "having an RGD sequence" as used herein may refer to originally having an RGD sequence or having an RGD sequence bound chemically. It is preferred that the first material having an RGD material be biodegradable.

Examples of the protein having an RGD sequence include a conventionally known adhesive protein or a water-soluble protein having an RGD sequence. Examples of the adhesive protein include fibronectin, vitronectin, laminin, cadherin, or collagen. Examples of the water-soluble protein having an RGD sequence include collagen bound to an RGD sequence, gelatin, albumin, globulin, proteoglycan, enzyme, or an antibody.

As the polymer having an RGD sequence, for example, there is given a naturally-derived polymer or a synthetic polymer. Examples of the naturally-derived polymer having an RGD sequence include water-soluble polypeptide, low-molecular-weight peptide, polyamino acid such as α-polylysine or ε-polylysine, and saccharide such as chitin or chitosan. Examples of the synthetic polymer having an RGD sequence include polymers or copolymers having an RGD sequence of a straight-chain type, a graft type, a comb type, a dendritic type, or a star type. Examples of the polymers or the copolymers include polyurethane, polycarbonate, polyamide, or copolymers thereof, polyester, poly(N-isopropylacrylamide-co-polyacrylic acid), polyamidoamine dendrimer, polyethylene oxide, poly ε-caprolactam, polyacrylamide, or poly(methyl methacrylate-γ-oxyethylene polymethacryate).

Of those described above, the first material is preferably fibronectin, vitronectin, laminin, cadherin, polylysine, elastin, collagen bound to an RGD sequence, gelatin bound to an RGD sequence, chitin, or chitosan; more preferably fibronectin, vitronectin, laminin, polylysine, collagen bound to an RGD sequence, or gelatin bound to an RGD sequence.

(Interacting Second Material)

The interacting second material refers to a protein or a polymer that interacts with the first material having an RGD sequence. The term "interact" as used herein means that the first material and the second material approach each other to such a degree that they can be bound to each other, adhere to each other, adsorb each other, and give/receive electrons with respect to each other, for example, due to an electrostatic interaction, a hydrophobic interaction, a hydrogen bond, a charge movement interaction, covalent bond formation, specific interaction between proteins, and/or Van der Waals force. It is preferred that the interacting second material be biodegradable.

Examples of the protein that interacts with the first material include collagen, gelatin, proteoglycan, integrin, enzyme, or an antibody. As the polymer that interacts with the first material, for example, there is given a naturally-derived polymer or a synthetic polymer. Examples of the naturally-derived polymer that interacts with the first material include water-soluble polypeptide, low-molecular-weight peptide, polyamino acid, elastin, heparin, saccharide such as heparin sulfate or dextran sulfate, and hyaluronic acid. Examples of the polyamino acid include polylysine such as α-polylysine or ε-polylysine, polyglutamic acid, or polyaspartic acid. Examples of the synthetic polymer that interacts with the first material include polymers or copolymers having an RGD sequence of a straight-chain type, a graft type, a comb type, a dendritic type, or a star type. Examples of the polymers or the copolymers include polyurethane, polyamide, polycarbonate, or copolymers thereof, polyester, polyacrylic acid, polymethacrylic acid, polyethylene glycol-grafted-polyacrylic acid, poly (N-isopropylacrylamide-co-polyacrylic acid), polyamidoamine dendrimer, polyethylene oxide, poly ε-caprolactam, polyacrylamide, and poly(methyl methacrylate-γ-oxyethylene polymethacryate).

Of those described above, the second material is preferably gelatin, dextran sulfate, heparin, hyaluronic acid, globulin, albumin, polyglutamic acid, collagen, or elastin; more preferably gelatin, dextran sulfate, heparin, hyaluronic acid, or collagen; still more preferably gelatin, dextran sulfate, heparin, or hyaluronic acid.

There is no particular limit to the combination of the first material and the second material as long as different materials interacting with each other are combined, and one of the first and second materials is a polymer or a protein having an RGD sequence and the other is a polymer or a protein interacting with the above-mentioned one of the first and second materials Examples of the combination of the first and second materials include fibronectin and gelatin; fibronectin and ε-polylysine; fibronectin and hyaluronic acid; fibronectin and dextran sulfate; fibronectin and heparin; fibronectfin and collagen; laminin and gelatin; laminin collagen; polylysine and elastin; vitronectin and collagen; and collagen bound to RGD or gelatin bound to RGD and collagen or gelatin. Of those, fibronectin and gelatin; fibronectin and ε-polylysine; fibronectin and hyaluronic acid; fibronectin and dextran sulfate; fibronectin and heparin; or laminin and gelatin are preferred. The combination of fibronectin and gelatin is more preferred. It should be noted that one kind of the first material and one kind of the second material may be used, or two or more kinds of the first material and two or more kinds of the second material may be used in a range exhibiting interaction.

(First Material Having Positive Charge)

The first material having positive charge refers to a protein or a polymer having positive charge. As the protein having positive charge, for example, a water-soluble protein is preferred. Examples of the water-soluble protein include basic collagen, basic gelatin, lysozyme, cytochrome c, peroxidase, or myoglobin. Examples of the polymer having positive charge include a naturally-derived polymer and a synthetic polymer. Examples of the naturally-derived polymer include water-soluble polypeptide, low-molecular-weight peptide, polyamino acid, and saccharide such as chitin or chitosan. Examples of the polyamino acid include polylysine such as poly(α-lysine) and poly(ε-lysine), polyarginine, or polyhistidine. Examples of the synthetic polymer include polymers or copolymers of a straight-chain type, a graft type, a comb type, a dendritic type, or a star type. Examples of the polymers or the copolymers include polyurethane, polyamide, polycarbonate, or copolymers thereof, polyester, polydiallyldimethylammonium chloride, polyallylamine hydrochloride, polyethyleneimine, polyvinylamine, or polyamidoamine dendrimer.

(Second Material Having Negative Charge)

The second material having negative charge refers to a protein or a polymer having negative charge. As the protein having negative charge, for example, a water-soluble protein is preferred. Examples of the water-soluble protein include acid collagen, acid gelatin, alubumin, globulin, catalase, β-lactoglobulin, thyroglobulin, α-lactoalbumin, or egg albumin. Examples of the polymer having negative charge include a naturally-derived polymer and a synthetic polymer. Examples of the naturally-derived polymer include water-soluble polypeptide, low-molecular-weight polypeptide, polyamino acid such as poly(β lysine), or dextran sulfate. Examples of the synthetic polymer include polymers or copolymers of a straight-chain type, a graft type, a comb type, a dendritic type, or a star type. Examples of the polymers or the copolymers include polyurethane, polyamide, polycarbonate, and copolymers thereof, polyester, polyacrylic acid, polymethacrylic acid, polystyrene sulfonic acid, polyacrylamidemethylpropane sulfonic acid, terminal-carboxylated polyethylene glycol, polydiallyldimethylammonium salt, polyarylamine salt, polyethyleneimine, polyvinylamine, or polyamidoamine dendrimer.

Examples of the combination of the first material having positive charge and the second material having negative charge include ε-polylysine salt and polysulfonate; ε-polylysine and polysulfonate; chitosan and dextran sulfate; polyallylamine hydrochloride and polystyrenesulfonate; polydiallyldimethylammonium chloride and polystyrenesulfonate; or polydiallyldimethylammonium chloride and polyacrylate. The combination of ε-polylysine salt and polysulfonate or polydiallyldimethylammonium chloride and polyacrylate is preferred. It should be noted that one kind of the first material having positive charge and one kind of the second material having negative charge may be used, or two or more kinds of the first material and two or more kinds of the second material may be used in a range exhibiting interaction.

The thickness of the coating film containing an extracellular matrix component is for example preferably 1 nm to $1\times10^3$ nm, more preferably 2 nm to $1\times10^2$ nm, and still more preferably 3 nm to $1\times10^2$ nm for the reason that a dermis tissue layer in which coated cells are laminated more densely is obtained. The thickness of the coating film containing an extracellular matrix component can be controlled appropriately, for example, by the number of films forming the coating film. The coating film containing an extracellular matrix component is not particularly limited. The coating film may be formed of one layer or a multi-layer including, for example, 3, 5, 7, 9, 11, 13, 15, or more layers. It should be noted that the thickness of the coating film is determined by the method described in the examples.

The coated cells can be prepared, for example, by bringing cells into contact with an extracellular matrix component. For the reason that the adhesiveness between adjacent coated cells in a dermis tissue layer is enhanced, and a dermis tissue layer in which the coated cells are laminated more densely is obtained, it is preferred that the coated cells be prepared by bringing cells into contact with the first material and the second material alternately. Thus, a coating film in which a film containing the first material and a film containing the second material are laminated alternately can be formed on the surface of each cell. The contact order is not particularly limited. For the reason that a dermis tissue layer in which the coated cells are laminated more densely is obtained, it is preferred to first bring cells into contact with the first material and then bring the cells into contact with the second material. It is more preferred to bring the cells into contact with the first material and the second material in the above-mentioned order alternately. It is still more preferred to bring the cells into contact with the first material and the second material in the above-mentioned order, and after that, finally bring the cells into contact with the first material.

Hereinafter, a method for preparing coated cells is described by way of an example of a method involving first bringing cells into contact with the first material and then bringing the cells into contact with the second material, and bringing them in the stated order alternately.

First, cells are brought into contact with the first material. As a result, a film containing the first material is formed on the surface of each cell, and the surface of the cell is covered with the film containing the first material. The cells can be brought into contact with the first material, for example, by applying or adding the first material to the cells, soaking the cells in a first material-containing liquid, dripping or spraying the first material-containing liquid to the cells, or the like. Of those, for the reason of ease of an operation, it is preferred that the cells be brought into contact with the first material by soaking the cells in the first material-containing liquid.

The contact conditions can be appropriately determined in accordance with, for example, a contact method, the kind of the first material and/or the cells, and the concentration of the first material-containing liquid. The contact time is, for example, 30 seconds to 24 hours, preferably 1 minute to 60 minutes, more preferably 1 minute to 15 minutes, still more preferably 1 minute to 10 minutes, further preferably 1 minute to 5 minutes. The temperature of an atmosphere and/or the temperature of the first material-containing liquid during contact are, for example, 4 to 60° C., preferably 20 to 40° C., more preferably 30 to 37° C.

It is appropriate that the first material-containing liquid contains the first material, and it is preferred that the liquid contain the first material and a solvent or a dispersed solvent (hereinafter, which may be also referred to as "solvent"). The content of the first material in the first material-containing liquid is, for example preferably 0.0001 to 1% by mass, more preferably 0.01 to 0.5% by mass, still more preferably 0.02 to 0.1% by mass. Examples of the solvent include aqueous solvents such as water, phosphate buffered saline (PBS), and a buffer solution. Examples of the buffer solution include Tris buffer solution such as Tris-HCl buffer solution, phosphate buffer solution, HEPES buffer solution, citric acid-phosphoric acid buffer solution, glycylglycine-sodium hydroxide buffer solution, Britton-Robinson buffer solution, or GTA buffer solution. The pH of the solvent is not particularly limited, and is, for example, 3 to 11, preferably 6 to 8, more preferably 7.2 to 7.4.

The first material-containing liquid may further contain a salt, and as necessary, may contain, for example, pharmaceutical compositions such as a cell growth factor, cytokine, chemokine, hormone, a biologically active peptide, therapeutic agents for diseases, a preventive, an inhibitor, an antimicrobial agent, or an antiinflammatory agent. Examples of the salt include sodium chloride, potassium chloride, sodium hydrogencarbonate, sodium acetate, sodium citrate, potassium chloride, sodium hydrogenphosphate, magnesium sulfate, sodium succinate, and the like. One kind or two or more kinds of the salt may be contained in the first material-containing liquid. Both a first liquid and a second liquid may contain a salt, or either one of the first and second liquids may contain a salt. Although the salt concentration in the first material-containing liquid is not particularly limited, it is, for example $1\times10^{-6}$ M to 2M, preferably $1\times10^{-4}$ M to 1 M, more preferably $1\times10^{-4}$ M to 0.05 M.

Then, the first material that has not been used for forming the film containing the first material is removed. In the case where the cells are brought into contact with the first material by soaking the cells in the first material-containing liquid, the first material can be removed, for example, by separating the cells from the first material-containing liquid by centrifugation and removing a supernatant. Thus, the cells, each of which is covered with the film containing the first material, can be obtained. Further, the first material may be removed, for example, by filtration or the like.

In addition to the removal of the first material, washing using the above-mentioned solvent may be performed. The washing can be performed, for example, by centrifugation, filtration, or the like. As a method using centrifugation, for example, there is given a method involving adding a solvent after removing a supernatant, followed by centrifugation and removal of a supernatant. It is preferred that a solvent used in the washing is the same as that used in the first material-containing liquid.

Then, the cells covered with the film containing the first material are brought into contact with the second material. As a result, a film containing the second material is formed on the surface of the film containing the first material, and the surface of each cell covered with the film containing the first material is covered with the film containing the second material. The cells can be brought into contact with the second material in the same way as in the contact of the first material with the cells, except that a material with which the cells are brought into contact is set to be the second material.

By repeatedly bringing the cells into contact with the first material or the second material alternately, a coating film containing an extracellular matrix component, in which the film containing the first material and the film containing the second material are laminated alternately, can be formed on the entire surface of the cells. It can be appropriately determined how many times the cells should be brought into contact with the first material or the second material, for example, depending on the thickness of the coating film containing an extracellular matrix component to be formed.

[Dermis Tissue Layer]

The dermis tissue layer includes coated cells laminated three-dimensionally. The thickness of the dermis tissue layer and the number of cells (number of layers) to be laminated in the dermis tissue layer are not particularly limited. The number of cells (number of layers) to be laminated in the dermis tissue layer is preferably 3 layers or more, more preferably 4 layers or more, still more preferably 5 layers or more, further preferably 6 layers or more, for example, from the viewpoint of causing the dermis tissue layer to exhibit the nature and/or functions equivalent to those of a biological tissue of a human or the like. Although there is no particular limit to the upper limit of the number of cells to be laminated, for example, the number of cells is 100 layers or less, 50 layers or less, 40 layers or less, 20 layers or less, or 10 layers or less.

The dermis tissue layer is formed by culturing coated cells. By culturing coated cells, each of which is obtained by covering a surface of a cell with a coating film containing an extracellular matrix component, the coated cells are integrated, and further, the coated cells adjacent to each other adhere to each other through the coating film containing an extracellular matrix component, with the result that a dermis tissue layer, in which the coated cells are laminated three-dimensionally, can be formed.

The coated cells are cultured, for example, by seeding the coated cells on a base, and performing incubation for a predetermined period of time. As a result of the incubation, the coated cells adjacent to each other through the coating film containing an extracellular matrix component adhere to each other, and the coated cells are laminated three-dimensionally. Further, the distances between adjacent coated cells become small, and thus a dermis tissue layer with a dense structure is formed. The conditions for the incubation are not particularly limited, and appropriately determined in accordance with the cells. The incubation temperature is, for example 4 to 60° C., preferably 20 to 40° C., more preferably 30 to 37° C. The incubation time is, for example 1 to 168 hours, preferably 3 to 24 hours, more preferably 3 to 12 hours. A medium is not particularly limited, and can be appropriately determined in accordance with the cells. Examples of the medium include Eagle's MEM medium, Dulbecco's Modified Eagle's medium (DMEM), Modified Eagle's medium (MEM), Minimum Essential medium, RDMI, GlutaMax medium, or serum-free medium.

The density of the coated cells during seeding can be appropriately determined in accordance with, for example, the number of cell layers included in a dermis tissue layer to be formed. The density is for example, $1 \times 10^2$ cells/cm$^3$ to $1 \times 10^9$ cells/cm$^3$, preferably $1 \times 10^4$ cells/cm$^3$ to $1 \times 10^8$ cells/cm$^3$, more preferably $1 \times 10^5$ cells/cm$^3$ to $1 \times 10^7$ cells/cm$^3$.

For the reason that it is easy to provide and handle air-liquid culture for inducing the differentiation of epidermis cells, the coated cells are cultured preferably on a membrane filter, more preferably on a culture plate including a membrane filter, still more preferably on a culture plate including a housing portion and a base portion, in which the base portion is a membrane filter. It is preferred that the housing portion be transparent. As the culture plate, a commercially available plate may be used. Examples of the commercially available plate include Transwell (registered trademark), Cell Culture Insert (trade name), and the like.

The pore diameter of the membrane filter is not particularly limited as long as culture cells can be held on the membrane filter, and is for example 0.1 µm to 2 µm, preferably 0.4 µm to 1.0 µm. Further, examples of the material for the membrane include polyethylene terephthalate (PET), polycarbonate, or polytetrafluoroethylene (PTFF).

The dermis tissue layer thus formed can hold a laminated structure of the cells and can be excellent in long-term stability, for example, even when the dermis tissue layer is stored for 2 or more weeks, preferably 3 or more weeks, more preferably 4 or more weeks, still more preferably 5 or more weeks, further preferably 6 or more weeks after being formed. The dermis tissue layer may be formed once or formed a plurality of times repeatedly. By forming the dermis tissue layer a plurality of times repeatedly, a multi-layered dermis tissue layer in which more cells are laminated can be formed.

[Epidermis Layer]

The epidermis layer can be formed by culturing epidermis cells on a dermis tissue layer, and subjecting the resultant epidermis cells to air-liquid culture to induce the differentiation of the epidermis cells. As the epidermis cells, for example, epidermis keratinized cells can be used.

For culturing the epidermis cells, for example, it is preferred to seed coated cells on a dermis tissue layer, and performing incubation for a predetermined period of time. The conditions for the incubation are not particularly limited and can be appropriately determined in accordance with the cells. The incubation temperature is, for example 4 to 60° C., preferably 20 to 40° C., more preferably 30 to 37° C. The incubation time is, for example 1 to 3 days, preferably 1 to 2 days.

The medium is not particularly limited and can be appropriately determined in accordance with the cells. Media to be used for growing epidermis cells are preferred. As the media to be used for growing epidermis cells, for example, there is given a serum-free medium. Examples of the serum-free medium include: an MCDB 153 medium; an EpiLife (registered trademark) medium; media obtained by modifying amino acid compositions and the like of the MCDB 153 medium and EpiLife medium; or media obtained by mixing a Dulbecco's Modified Eagle's medium (DMEM) and a Ham's F-12 medium in a predetermined ratio. Examples of the media obtained by modifying the amino acid composition of the MCDB 153 medium include MCDB 153 modified media obtained by modifying the amino acid ratio of the MCDB 153 medium so that L-aspartic acid (salt) becomes 1.5 to 4 times, L-isoleucine (salt) becomes 22 to 26 times, L-glutamine (salt) becomes 1.5 to 3 times, L-glutamic acid (salt) becomes 1.1 to 2 times, L-tyrosine (salt) becomes 3 to 6 times, L-tryptophan (salt) becomes 5 to 7 times, L-valine (salt) becomes 0.4 to 0.7 times, L-histidine (salt) becomes 2 to 4 times, L-proline (salt) becomes 0.4 to 0.7 times, L-phenylalanine (salt) becomes 4 to 7 times, L-methionine (salt) becomes 4 to 6 times, and L-lysine (salt) becomes 1.1 to 2 times, and setting the content of L-glutamine (salt) in the total amino acid to be 65% by weight or more (for example, JP 2005-269923 A). It should be noted that the amino acid composition of the MCDB 153 medium is as shown in Table 1.

TABLE 1

| Amino acid | Ratio (mg/L) |
|---|---|
| L-arginine hydrochloride | 210.67 |
| L-asparagine (monohydrate) | 15 |
| L-aspartic acid | 3.99 |
| L-cysteine hydrochloride | 37.83 |
| L-glutamic acid | 14.7 |
| L-glutamine | 876 |
| glycine | 7.51 |
| L-histidine | 12.42 |
| L-isoleucine | 1.97 |
| L-leucine | 65.6 |
| L-lysine hydrochloride | 18.27 |
| L-methionine | 4.48 |
| L-phenylalanine | 4.95 |
| L-proline | 34.54 |
| L-serine | 63.05 |
| L-threonine | 11.9 |
| L-tryptophane | 3.06 |
| L-tyrosine | 2.72 |
| L-valine | 35.15 |

The medium may contain, for example, salts or vitamins. Examples of the salts include potassium chloride, sodium chloride, magnesium chloride, disodium hydrogenphosphate, and the like. Examples of the vitamins include choline chloride, cyanocobalamin, nicotinamide, D-pantothenic acid or a salt thereof, pyridoxine hydrochloride or pyridoxal hydrochloride, D-biotin, thiamine hydrochloride, riboflavine, folic acid, DL-α-lipoic acid, or myoinositol.

The density of the epidermis cells during seeding is, for example $1 \times 10^2$ cells/cm$^2$ to $1 \times 10^9$ cells/cm$^2$, preferably $1 \times 10^4$ cells/cm$^2$ to $1 \times 10^8$ cells/cm$^2$, more preferably $1 \times 10^5$ cells/cm$^2$ to $1 \times 10^7$ cells/cm$^2$.

The air-liquid culture is performed by changing a medium to a keratinized medium, and thereafter, performing incubation while exposing the surfaces of the epidermis cells to air. The incubation temperature is, for example 4 to 60° C., preferably 20 to 40° C., more preferably 30 to 37° C. The incubation time is, for example 1 to 40 days, preferably 5 to 30 days, more preferably 7 to 10 days. As the keratinized medium (stratified medium), a medium obtained by adding, for example, calcium and/or fetal bovine serum to the above-mentioned medium used for growing epidermis cells, or the like can be used. It is preferred that the concentration of calcium of the medium be, for example about 0.4 mM to 2.0 mM.

It is preferred to form a film composed of an extracellular matrix component on a dermis tissue layer prior to seeding the epidermis cells. Thus, the adhesiveness between the dermis tissue layer and the epidermis layer can be further enhanced. The film composed of an extracellular matrix component can be formed by bringing the first material-containing liquid and the second material-containing liquid into contact with the dermis tissue layer alternately. The first material-containing liquid and the second material-containing liquid can be brought into contact with the dermis tissue layer, for example, by coating, soaking, dripping, or spraying.

The method for producing an artificial skin model of the present invention may include forming a tissue ancillary organ in a dermis tissue layer. The tissue ancillary organ can be formed, for example, by culturing a mixture of cells forming the tissue ancillary organ and coated cells (for example, fibroblasts or the like) for forming a dermis tissue layer in forming the dermis tissue layer, or by culturing cells forming the tissue ancillary organ, arranged between cell layers in which coated cells for forming the dermis tissue layer are laminated, or the like. The cells forming the tissue ancillary organ can be arranged between the cell layers, for example, by arranging the cells forming the tissue ancillary organ on a cell layer in which coated cells are laminated; as necessary culturing the cells for a predetermined period of time; and arranging the coated cells on the arranged cells; and the like. Therefore, the method for producing an artificial skin model of the present invention may include: forming a cell layer in which cultured coated cells are laminated in forming a dermis tissue layer; arranging cells forming a tissue ancillary organ on the cell layer; and arranging the coated cells on the cell layer in which the cells forming the tissue ancillary organ are arranged, and culturing the coated cells to form a cell layer in which the coated cells are laminated.

In the case of forming an organ to be formed in a tissue like a mesh such as a blood vessel and a lymphatic vessel as a tissue ancillary organ, it is preferred that the tissue ancillary organ be formed by culturing the cells forming the tissue ancillary organ in such a manner that the cells forming the tissue ancillary organ are sandwiched between cell layers in which coated cells are laminated. Thus, by culturing the cells forming the tissue ancillary organ while the cells are sandwiched between the cell layers, a dense blood vessel network or lymphatic vessel network closer to a living body of a human can be formed. In the case of forming a blood vessel as a tissue ancillary organ, it is appropriate that vascular endothelial cells are used as the cells forming the tissue ancillary organ. In the case of forming a lymphatic vessel as a tissue ancillary organ, it is appropriate that lymphatic vessel endothelial cells are used as the cells forming the tissue ancillary organ.

The cells forming a tissue ancillary organ are as described above. Further, in addition to or instead of the cells forming a tissue ancillary organ, stem cells and/or precursor cells of the cells forming the tissue ancillary organ may be used. In the same way as in coated cells to be used for forming a dermis tissue layer, as the cells forming the tissue ancillary organ, cells each of which is obtained by covering a surface of a cell with the coating film containing an extracellular matrix component may be used, or the cells may be used without being covered with a coating film in the same way as in the formation of an epidermis layer. From the viewpoint of enhancing operation efficiency, cells each of which is obtained by covering a surface of a cell with the coating film containing an extracellular matrix component is preferred. The number of cells to be seeded, the culture conditions, and the like can be appropriately determined in accordance with cells forming a tissue ancillary organ, and the like. The coating film containing an extracellular matrix component can be formed in the same way as in the above-mentioned coated cells.

Hereinafter, the method for producing an artificial skin model of the present invention is described with reference to the drawings by way of an exemplary embodiment using a plate (cell culture insert) having a membrane filter as a base. FIG. 1 shows schematic views of an example of the method for producing an artificial skin model of the present invention.

First, coated cells 1, each cell surface 3 of which is covered with a coating film 2 containing an extracellular matrix component, are seeded in a cell culture insert 4, and then, a medium 6 is added into a well 5 in which the cell culture insert 4 is arranged. In this state, the coated cells 1 are cultured for a predetermined period of time. As shown in FIG. 1(a), at an initial stage of the culture, the coated cells 1 are dispersed in the medium 6 in the cell culture insert 4. As the culture proceeds, the coated cells 1 are integrated on a bottom surface of the cell culture insert 4, and the adjacent coated cells 1 adhere to each other through intermediation of the coating film 2. Thus, as shown in FIG. 1(b), a dermis tissue layer 7 in which the coated cells 1 are laminated three-dimensionally is formed.

Then, epidermis cells 8 are seeded on the dermis tissue layer 7 (FIG. 1(c)), and the epidermis cells are cultured for a predetermined period of time. As the culture proceeds, the epidermis cells 8 are arranged so as to be laminated on the dermis tissue layer 7 (FIG. 1(d)). Prior to seeding the epidermis cells, it is preferred that a film containing an extracellular matrix component be formed on the dermis tissue layer (not shown). This can enhance the adhesiveness between the dermis tissue layer and the epidermis cells.

Then, the medium is changed to a keratinized medium 9, and air-liquid culture is performed for a predetermined period of time. The air-liquid culture can be performed, for example, by arranging the cell culture insert 4 on a platform 11 on which filter paper 10 is disposed so that a membrane filter portion of the cell culture insert 4 is positioned on an air-liquid interface, as shown in FIG. 1(e), and performing incubation in this state. The incubation is performed under the condition that, of the epidermis cells arranged on the dermis tissue layer 7, epidermis cells positioned in the vicinity of the surface are exposed to air, whereby the differentiation of the epidermis cells on the surface is induced, and the epidermis cells are keratinized to become a keratinized layer 13, with the result that an epidermis layer 12 is formed (for example, FIG. 1(f)).

[Artificial Skin Model]

As another aspect, the present invention relates to an artificial skin model produced by the production method of the present invention. The artificial skin mode of the present invention includes a dermis tissue layer including coated cells, each of which is obtained by covering a surface of a cell with a coating film containing an extracellular matrix component, and an epidermis layer formed on the dermis tissue layer. In the artificial skin model of the present invention, for example, evaluations of a drug effect test, a pharmacological test, and a safety test of a test substance can be performed in an environment close to an actual skin. Further, the artificial skin model of the present invention can also be used as a covering material for treating, for example, a burn or a wound.

In the epidermis layer, for example, it is preferred that a tight junction be formed between adjacent epidermis cells. When a tight junction is formed in the epidermis layer, the barrier function and the like of the epidermis layer can be evaluated by measuring a TER.

It is preferred that the artificial skin model of the present invention include a tissue ancillary organ formed in the dermis tissue layer. This enables the evaluations of a drug effect test, a pharmacological test, and/or a safety test to be performed in an environment closer to an actual skin.

The number of cells to be laminated in the dermis tissue layer is not particularly limited. From the viewpoint of allowing the nature and functions equivalent to those of a skin of a human or the like to be exhibited, the number of cells to be laminated is preferably 3 layers or more, more preferably 4 layers or more, still more preferably 5 layers or more, further preferably 6 layers or more. Although there is no particular upper limit to the number of cells to be laminated, for example, the upper limit is 100 layers or less, 50 layers or less, 40 layers or less, 20 layers or less, or 10 layers or less.

[Evaluation Method]

In still another aspect, the present invention relates to a method for evaluating irritation of a test substance with respect to a skin through use of the artificial skin model of the present invention. The evaluation method of the present invention can exhibit, for example, the effect of evaluating a test substance in an environment close to an actual skin compared with a conventional method. Further, the evaluation method of the present invention can be a very useful tool in, for example, pharmacokinetic evaluation of drugs having various molecular weights in creating (screening) new drugs or the like, and evaluation in development of cosmetic products, nonmedicinal products, and the like.

The evaluation method of the present invention can be performed, for example, by bringing a test substance into contact with the artificial skin model, and measuring a response of the artificial skin model to stimulation caused by the contact with the test substance. The response can be measured, for example, by measuring a TER or the like. The test substance refers to a substance to be evaluated, and for example, there are given an inorganic compound, and an organic compound.

[Evaluation Kit]

In still another aspect, the present invention relates to an evaluation kit for evaluating irritation of a test substance. The evaluation kit of the present invention includes the artificial skin model of the present invention. The evaluation kit of the present invention enables, for example, the evaluation method of the present invention to be performed more easily.

The evaluation kit may further include a product containing at least one of a reagent, a material, a tool, and a device to be used for a predetermined inspection, and an instruction (operation manual) regarding the evaluation.

[Artificial Skin Model Production Kit]

In still another aspect, the present invention relates to an artificial skin model production kit. It is preferred that the artificial skin model production kit of the present invention include, for example, a reagent used for forming a coating film containing an extracellular matrix component, and an instruction describing a method for producing the artificial skin model of the present invention. The artificial skin model production kit of the present invention enables the artificial skin model of the present invention to be produced more easily.

The artificial skin model production kit of the present invention may further include a base in which a dermis tissue layer is formed. When the artificial skin model production kit includes a base in which a dermis tissue layer is formed, for example, the artificial skin model of the present invention can be produced more easily within a short period of time, and further, time required until a tissue ancillary organ is formed can be shortened.

EXAMPLES

The thickness of a coating film of coated cells, and the thickness of a three-dimensional tissue were measured as follows.

[Thickness of a Coating Film]

The thickness of a coating film containing an extracellular matrix component formed on a cell surface was determined by separately forming a coating film on a base, counting the number of conducted treatments (steps) and measuring the thickness of a coating film formed by the steps through use of a quartz crystal microbalance (QCM) measurement method, and from those results, calculating the thickness of the coating film in accordance with the number of steps conducted during formation of the coating film on the cell surface. The measurement using the QCM measurement method was performed as follows. A QCM quartz crystal sensor was washed with a piranha solution for 1 minute; after that, the QCM quartz crystal sensor was soaked in 50 mM Tris buffer solution (pH 7.4) of 0.2 mg/mL of fibronectin (hereinafter, which may be also referred to as "FN") at 37° C. for 1 minute; the QCM quartz crystal sensor was washed with 50 mM Tris buffer solution (pH 7.4) and dried by air; and then, a frequency shift was measured (Step 1). Then, the QCM quartz crystal sensor was soaked in 50 mM Tris buffer solution (pH 7.4) of 0.2 mg/mL of gelatin (hereinafter, which may be also referred to as "G") at 37° C. for 1 minute; the QCM quartz crystal sensor was washed with 50 mM Tris buffer solution (pH 7.4) and dried by air; after that, a frequency shift was measured (Step 2). By repeating Steps 1 and 2 alternately, a coating film was formed on the QCM quartz crystal sensor, and a frequency shift was also measured. Based on the obtained frequency shift, the number of steps and the thickness of the coating film formed by the steps were obtained.

[Thickness of a Three-dimensional Tissue (Dermis Tissue Layer)]

The thickness of a three-dimensional tissue was measured by producing a slice of a three-dimensional tissue (dermis tissue layer), subjecting the produced slice to hematoxylin-eosin (HE) staining, and thereafter, observing the slice with a microscope.

Experimental Example 1

[Relationship Between the Seeded Cell Number and the Layer Number of Laminated Cells or the Yield]

Coated cells, each of which was obtained by covering a surface of a cell with a coating film containing an extracellular matrix component, were prepared, and the obtained coated cells were cultured to form a three-dimensional tissue in which the coated cells were laminated. A relationship between the seeded cell number and the layer number of laminated cells, and a relationship between the seeded cell number and the yield were evaluated.

[Preparation of Coated Cells]

As a coating film containing an extracellular matrix component, a film was formed, in which a film containing a first material and a film containing a second material were laminated alternately. As the first material, fibronectin derived from bovine plasma (Commodity code: F4759, manufactured by Sigma-Aldrich Corporation) was provided. As the second material, gelatin (Commodity code: 077-03155, manufactured by Wako Pure Chemical Industries, Ltd.) was provided. As the cells, human fibroblasts (Normal Human Dermal Fibroblasts (NHDF), manufactured by Cambrex Corporation) were provided.

1 mL of 50 mM Tris buffer solution (pH 7.4) of 0.2 mg/mL of fibronetin was added to $5 \times 10^6$ cells of human fibroblasts, and the resultant was incubated at 37° C. for 1 minute. After that, the resultant was centrifuged at 2,000 rpm for 2 minutes, and a supernatant was removed. Then, 1 mL of 50 mM Tris buffer solution (pH 7.4) was added to the resultant to wash it for 1 minute. After that, the resultant was centrifuged at 2,000 rpm for 2 minutes, and a supernatant was removed. 50 mM Tris buffer solution (pH 7.4) of 0.2 mg/mL of gelatin was added to the resultant, and the resultant was incubated at 37° C. for 1 minute. After that, the resultant was centrifuged at 2,000 rpm for 2 minutes, and a supernatant was removed. 1 mL of 50 mM Tris buffer solution (pH 7.4) was added to the resultant to wash it for 1 minute. After that, the resultant was centrifuged at 2,000 rpm for 2 minutes, and a supernatant was removed. One step was defined to include incubation and washing with a fibronectin-containing solution, and incubation and washing with a gelatin-containing solution. Four steps were performed, and thereafter, incubation and washing with a fibronectin-containing solution were performed. As a result, a coating film ((FN/G)$_4$FN film) including a film composed of 5 layers of fibronectin and a film composed of 4 layers of gelatin, in which these layers were laminated alternately, was formed on a human fibroblast surface. The thickness of the coating film formed on the cell surface was 6 nm.

[Production of a Three-dimensional Tissue]

First, $1 \times 10^6$ cells of human fibroblasts, each of which was covered with a (FN/G)$_4$FN film, were seeded onto a membrane filter of a cell culture insert (Catalog No.: 353090, manufactured by Becton, Dickinson and Company; pore size: 0.4 µm, surface area: 4.2 cm$^2$) arranged on a 6-well culture plate. An Eagle's MEM medium containing 10% by weight of fetal bovine serum was added, and the human fibroblasts were cultured at 37° C. for 1 day. As a result, a three-dimensional tissue (thickness: 35 µm) in which 8 layers of human fibroblasts were laminated was obtained.

A three-dimensional tissue was produced by performing culture under the same conditions as those in the above except that the number of cells to be seeded was set to $0.1 \times 10^6$ cells, $0.5 \times 10^6$ cells, $2 \times 10^6$ cells, $3 \times 10^6$ cells, $4 \times 10^6$ cells, $5 \times 10^6$ cells, or $10 \times 10^6$ cells. Table 2 and FIG. 2 show a relationship between the seeded cell number and the layer number of laminated cells, and a relationship between the seeded cell number and the yield, based on the obtained three-dimensional tissue. It should be noted that the yield (%) was calculated from the following expression based on the number of living cells collected from the obtained three-dimensional tissue and the seeded cell number.

Yield(%)=(Number of living cells collected from three-dimensional tissue/seeded cell number)× 100

The collection of cells from the three-dimensional tissue and the measurement of the number of living cells were performed as follows.

First, 1 mL of PBS containing 0.1% trypsin was added to the obtained three-dimensional tissue. The resultant was allowed to stand still for about 5 minutes to isolate cells from the three-dimensional tissue, and the isolated cells were collected by centrifugation. PBS containing 3% trypan blue was added to the collected cells, and the number of living cells was measured through use of a hemacytometer under a phase-contrast microscope.

TABLE 2

|  |  | Layer number of laminated cells (layer) | Thickness (µm) | Yield (%) |
|---|---|---|---|---|
| Seeded cell number (cells) | $0.1 \times 10^6$ | 1 | 4 | 105 |
|  | $0.5 \times 10^6$ | 2 | 11 | 101 |
|  | $1 \times 10^6$ | 4 | 18 | 96 |
|  | $2 \times 10^6$ | 8 | 35 | 99 |
|  | $3 \times 10^6$ | 3 | 19 | 102 |
|  | $4 \times 10^6$ | 2 | 13 | 83 |
|  | $5 \times 10^6$ | 1 | 10 | 34 |
|  | $10 \times 10^6$ | 2 | 8 | 12 |

Figure 2B:
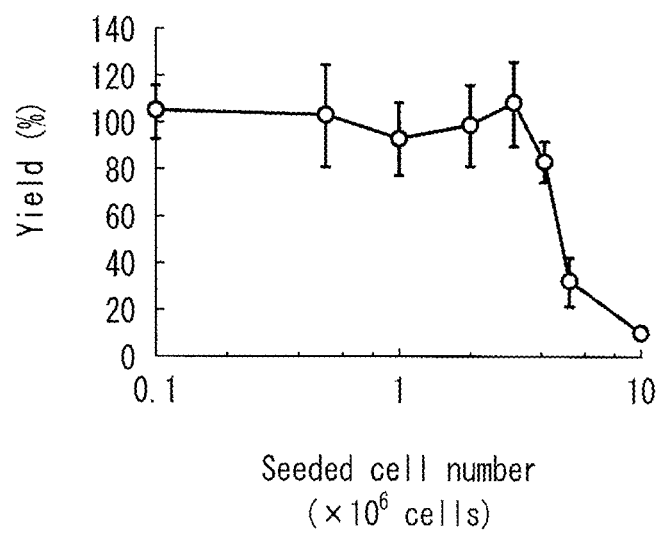
FIG. 2B is an example of a graph showing a relationship between the seeded cell number and the yield.

FIG. 2A is a graph showing a relationship between the seeded cell number and the layer number of laminated cells, and FIG. 2B is a graph showing a relationship between the seeded cell number and the yield. As shown in Table 2 and FIG. 2A, in the case where the seeded cell number was in a range of $2 \times 10^6$ cells or less, the layer number of laminated cells increased in accordance with the seeded cell number. Further, as shown in Table 2 and FIG. 2B, in the case where the seeded cell number was in a range of $3 \times 10^6$ cells or less, the yield of 90% or more was exhibited.

Experimental Example 2

[Stability of a Three-dimensional Tissue Structure]

Coated cells were provided and a three-dimensional tissue was produced in the same way as in Experimental Example 1, and a three-dimensional tissue in which NHDF was laminated in 1 layer, 2 layers, or 5 layers was produced. The obtained three-dimensional tissue was cultured at 37° C. for 28 days in DMEM medium containing 10% fetal bovine serum, and the amount of DNA in the three-dimensional tissue and the thickness of the three-dimensional tissue were measured. FIG. 3 shows the results. It should be noted that the DNA amount was measured by DNeasy Blood & Tissue Kit (trade name, manufactured by QUIAGEN GmbH).

Figure 3A:
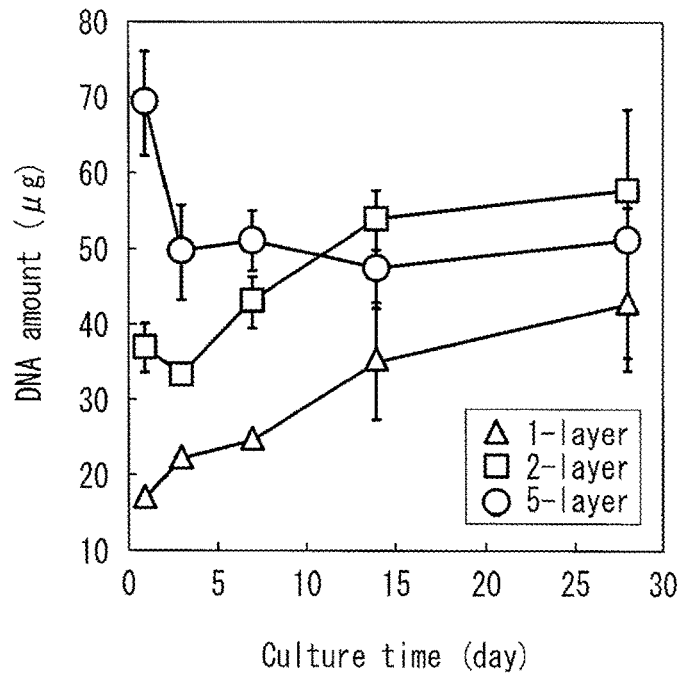
FIG. 3A is an example of a graph showing a relationship between the culture time and the DNA amount.
Figure 3B:
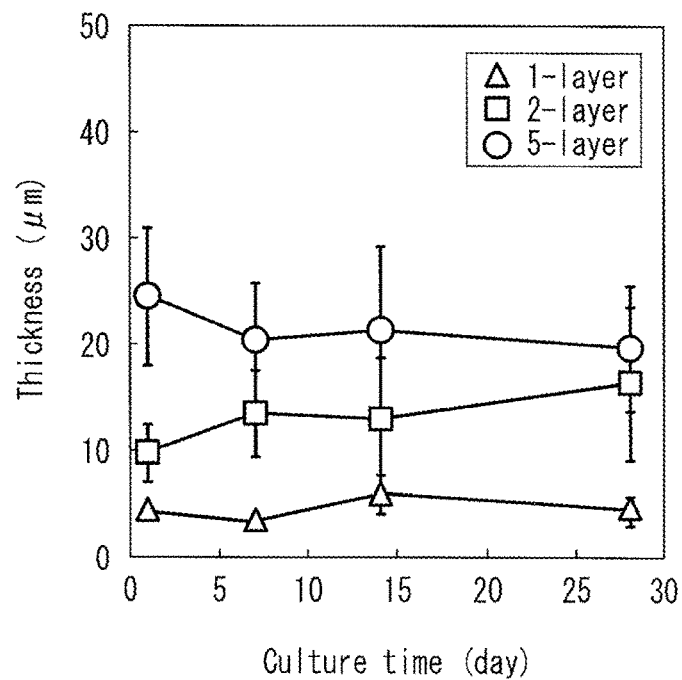
FIG. 3B is an example of a graph showing a relationship between the culture time and the thickness of a three-dimensional tissue.

FIG. 3A is a graph showing a relationship between the culture time and the DNA amount, and FIG. 3B is a graph showing a relationship between the culture time and the thickness of the three-dimensional tissue. In FIGS. 3A and 3B, triangular marks indicate results of a three-dimensional tissue including 1 NHDF layer; rectangular marks indicate results of a three-dimensional tissue including 2 NHDF layers; and circular marks indicate results of a three-dimensional tissue including 5 NHDF layers. As shown in FIGS. 3A and 3B, even when one month has elapsed after the three-dimensional tissue was produced, it was confirmed that the laminated structure of cells was kept.

Example 1

An artificial skin model was produced in which an epidermis layer was formed on a dermis tissue layer in which NHDF was laminated in 8 layers.

(Formation of a Dermis Tissue Layer)

A dermis tissue layer in which NHDF was laminated in 8 layers was formed by performing culture for 1 day under the conditions similar to those of Experimental Example 1 except that the number of NHDF, each surface of which was covered with an (FN/G)$_4$FN film, to be seeded was set to 2×10$^6$ cells.

[Formation of an Epidermis Layer]

50 mM Tris buffer solution (pH 7.4) of 0.2 mg/mL of fibronectin and 50 mM Tris buffer solution (pH 7.4) of 0.2 mg/mL of gelatin were alternately added four times respectively to the surface of the obtained dermis tissue layer. After that, 50 mM Tris buffer solution (pH7.4) of 0.2 mg/mL of fibronectin was added to the surface of the dermis tissue layer to form an (FN/G)$_4$FN film. 6×10$^5$ cells of keratinocytes (KC) were seeded on the surface of the dermis tissue layer on which the (FN/G)$_4$FN film was formed and cultured at 37° C. for 2 days. Then, the medium was changed to a keratinized medium (stratified medium), and a cell culture insert was arranged so that a membrane filter of the cell culture insert was positioned on an air-liquid interface of the keratinized medium. In this state, air-liquid culture was performed for 10 days to induce differentiation, whereby an artificial skin model was produced. The air-liquid culture was performed at 37° C. The medium was changed one every day from the start of culture.

The obtained artificial skin model and its three-dimensional culture construct before the differentiation induction (cultured for 2 days after seeding) were respectively subjected to HE staining, and FIG. 4 shows photographs obtained by observing the artificial skin model and the culture construct with a microscope. FIG. 4A is a photomicrograph before the differentiation induction, and FIG. 4B is a photomicrograph of the obtained artificial skin model. As shown in FIG. 4B, an artificial skin model including a dermis tissue layer in which NHDF was laminated and an epidermis layer formed on the surface of the dermis tissue layer was produced by the method of the present invention.

Example 2

An artificial skin model was produced in the same way as in Example 1, except that, in formation of a dermis tissue layer, the number of NHDF to be seeded was set to 1×10$^6$ cells, and the layer number of NHDF to be laminated in a dermis tissue layer was set to four. FIG. 5 shows microphotographs after HE staining of the obtained artificial skin model and the artificial skin model before differentiation induction (cultured for 2 days after seeding). FIG. 5A is a microphotograph before differentiation induction, and FIG. 5B is a microphotograph of the artificial skin model

Example 3

An artificial skin model was produced in the same way as in Example 1, except that, in formation of a dermis tissue layer, the number of NHDF to be seeded was set to 0.5×10$^6$ cells, and the layer number of NHDF to be laminated in a dermis tissue layer was set to two. FIG. 6 shows microphotographs after HE staining of the obtained artificial skin model and the artificial skin model before differentiation induction (cultured for 2 days after seeding). FIG. 6A is a microphotograph before differentiation induction, and FIG. 6B is a microphotograph of the artificial skin model.

Comparative Example 1

A cultured skin was created by forming an epidermis layer on a collagen gel used as a support. First, DMEM solution (Solution I) containing Cell matrix type I-A (manufactured by Nitta Gelatin Inc.) and 20% fetal bovine serum was produced, and about 0.25 mL of the DMEM solution (Solution I) was poured into a cell culture insert. The cell culture insert was allowed to stand still in an incubator for 5 minutes. About 0.75 mL of the solution I in which NHDF was added in a concentration of 5×10$^5$ cells/mL was added to the cell culture insert. The cell culture insert was allowed to stand still in an incubator for 30 minutes, whereby the solution I containing NHDF was gelled. Then, collagen gel containing NHDF was cultured for 5 days in DMEM containing ascorbic acid. After that, keratinocytes were seeded and allowed to adhere to the surface of the collagen gel in the same way as in Example 1 to induce differentiation, and thus a cultured skin was obtained. FIG. 7 shows a picture of the obtained cultured skin.

In the case where an epidermis layer was formed through use of a collagen gel as a support, due to the contraction of the collagen gel, peeling of the collagen gel in an outer edge portion of the cell culture insert and a portion in which epidermis cells were not present on the collagen gel were observed as shown in FIG. 7. In contrast, according to the method of the present invention, a collagen gel was not used as a support, and hence the deviation of the cells caused by the contraction of the collagen gel did not occur, with the result that an artificial skin model in which cells were arranged uniformly was produced.

Reference Example 1

An epidermis layer was formed in the same way as in Example 1 except that 6 ×10$^5$ cells of keranocytes were seeded on a membrane filter of a cell culture insert without forming a dermis tissue layer. FIG. 8 shows microphotographs after HE staining of the obtained cultured skin and the cultured skin before differentiation induction (cultured for 2 days after seeding). FIG. 8A is a microphotograph before differentiation induction, and FIG. 8B is a microphotograph of the obtained cultured skin.

Example 4

[Evaluation of a Barrier Function]

The artificial skin models of Examples 1 to 3 and the cultured skins of Comparative Example 1 and Reference Example 1 were evaluated for a barrier function by measuring a transepithelial electric resistance (TER).

A cell culture insert, in which an artificial skin model or a cultured skin was arranged, was put in a well with phosphate buffer solution (pH 7.4) added thereto. Electrodes were arranged respectively in an inner portion and an outer portion (within the well) of the cell culture insert, and a resistance was measured by applying a voltage between the electrodes. The obtained resistance was defined as a TER (Ω). The culture for providing the obtained artificial skin model and cultured skin was performed in a keratinized medium at 37° C. A TER was measured one every day from the start of the culture. FIG. 9 shows the results in a graph.

Figure 9A:
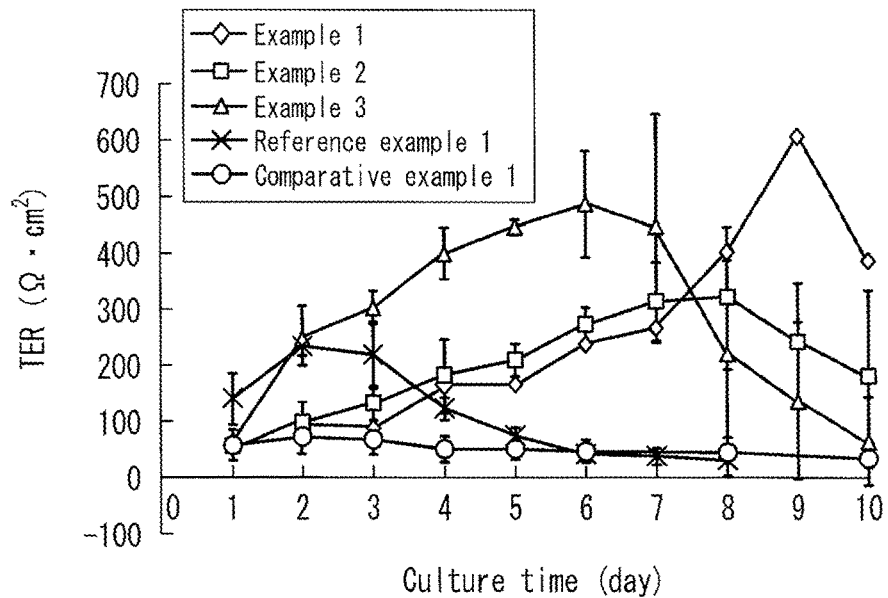
FIG. 9A is an example of a graph showing a relationship between the culture time and the transepithelial electric resistance (TER) of an artificial skin model or a cultured skin.
Figure 9B:
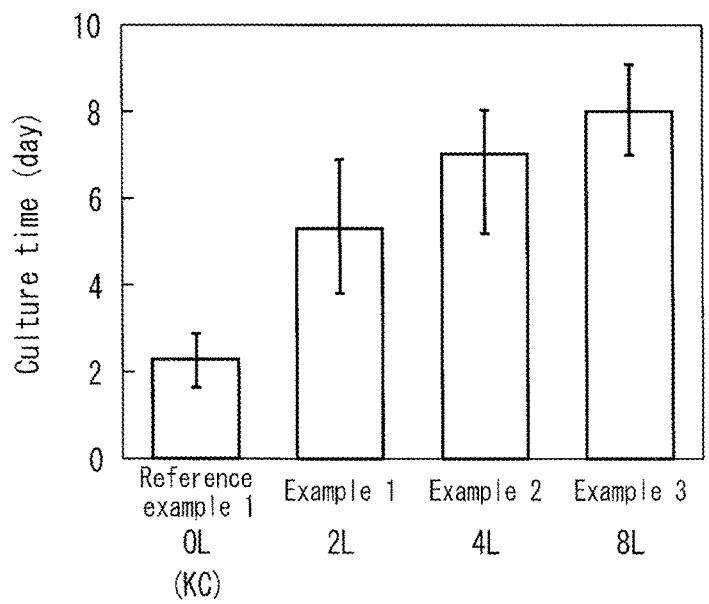
FIG. 9B is an example of a graph showing a relationship between the layer number of cells in a dermis tissue layer and the maximum day of the TER.

FIG. 9A is a graph showing a relationship between the culture time of the artificial skin model or the cultured skin and the TER, and FIG. 9B is a graph showing a relationship between the layer number of NHDF in a dermis tissue layer and the maximum day of the TER. In FIG. 9A, diagonal marks indicate the results of Example 1 (NHDF 8 layers+KC), rectangular marks indicate the results of Example 2 (NHDF 4 layers+KC), triangular marks indicate the results of Example 3 (NHDF 2 layers+KC), X marks indicate the results of Reference Example 1 (only KC), and circular marks indicate the results of Comparative Example 1 (collagen gel+KC). As shown in FIG. 9A, the artificial skin models of Examples 1 to 3 had a high TER, compared with the cultured skin of Comparative Example 1 in which an epidermis layer was formed on a collagen gel. It can be said from the foregoing that a tight junction was formed between adjacent epidermis cells in an epidermis layer in the artificial skin models of Examples 1 to 3. Thus, it was suggested that an artificial skin model capable of being evaluated for a barrier function of a skin can be provided according to the present invention.

Further, as shown in FIG. 9B, the maximum day of a TER increased along with an increase in layer number of human skin fibroblasts in a dermis tissue layer. This suggested that, by increasing the layer number of human skin fibroblasts laminated in a dermis tissue layer, the turnover of the human skin fibroblasts approaches the turnover (differentiation time, 28 days) of a living skin.

It should be noted that in a three-dimensional tissue of only a dermis tissue layer, a TER was almost 0 irrespective of the layer number of laminated NHDF (date not shown).

Example 5

An artificial skin model including blood capillaries was produced. As vascular endothelial cells, human umbilical vein endothelial cells (HUVEC) were used.

First, NHDF covered with an $(FN/G)_4FN$ coating film, and HUVEC covered with an $(FN/G)_4FN$ coating film were provided. The HUVEC covered with an $(FN/G)_4FN$ coating film was obtained by forming an $(FN/G)_4FN$ coating film on the surface of HUVEC in the same procedure as that of Experimental Example 1 except for using HUVEC instead of NHDF. It should be noted that the NHDF covered with an $(FN/G)_4FN$ coating film was colored with a green fluorochrome (trade name: Cell Tracker™ Green Fluorescent Probe, Product code: PA-3011, manufactured by Takara Bio Inc.).

Next, $1\times10^6$ cells of the NHDF covered with an $(FN/G)_4FN$ coating film were seeded and cultured at 37° C. for 1 day in the same way as in Experimental Example 1, whereby a first dermis tissue layer in which NHDF was laminated in four layers was formed. An $(FN/G)_4FN$ film was formed on the surface of the obtained first dermis tissue layer in the same way as in forming an epidermis layer of Example 1, and $2\times10^5$ cells of the HUVEC covered with an $(FN/G)_4FN$ coating film were seeded on the $(FN/G)_4FN$ film formed on the first dermis tissue layer. The HUVEC was cultured at 37° C. for 1 day to form one HUVEC layer on the dermis tissue layer. An $(FN/G)_4FN$ film was formed on the surface of the HUVEC layer in the same way as in forming an epidermis layer of Example 1, and $1\times10^5$ cells of the NHDF covered with an $(FN/G)_4FN$ coating film were seeded on the $(FN/G)_4FN$ film formed on the HUVEC layer. The NHDF was cultured at 37° C. for 1 day in the same way as in Example 1, whereby a second dermis tissue layer in which the NHDF was laminated in four layers was formed. Then, an epidermis layer was formed on the surface of the second dermis tissue layer in the same way as in Example 1. After forming the epidermis layer, culture was performed in a keratinized medium at 37° C. for 7 days to obtain an artificial skin model. Then, regarding the obtained artificial skin model, the HUVEC was subjected to immunostaining through use of monoclonal mouse anti-human CD31 antibodies (Product code: JC70A, manufactured by Dako Corporation) and Goat anti-mouse Alexa Flour 546-confugated IgG antibodies (Product code: A11001, manufactured by Invitrogen Corporation).

Figures 10A, 10B:
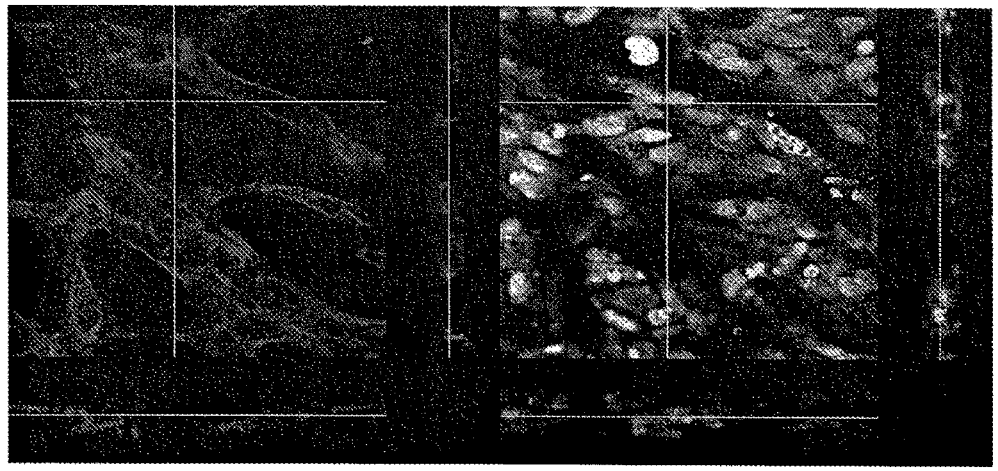
FIG. 10 shows an example of confocal laser scanning microscope (CLSM) images of an artificial skin model of Example 5.

FIG. 10 shows an example of confocal laser scanning microscope (CLSM) images of the obtained artificial skin model. FIG. 10 shows CLSM images of the obtained artificial skin model. FIG. 10A shows an image of HUVEC stained in red, and FIG. 10B shows an image of NHDF stained in green.

Cells derived from the HUVEC that had been positioned on the surface of the first dermis tissue layer in the form of pavement stones before the culture changed to a capillary form by performing culture under the condition that the HUVEC layer was interposed between the first dermis tissue layer and the second dermis tissue layer. When the culture was performed for further 7 days, the cells derived from the HUVEC came to form a tube structure, and the formed tubes were connected to each other, whereby blood capillaries having a tube structure were formed in the artificial skin model as shown in FIG. 10. Further, the formed blood capillaries were dense. In the case where the blood capillaries were observed in a cross-section taken along a lateral direction (planar direction) of the artificial skin model, the proportion of an area occupied by the blood capillaries in that plane was about 45 to 60%, and the distance of the blood capillaries adjacent to each other was 50 to 100 µm.

Further, it was confirmed that very dense blood capillaries were formed by performing culture under the condition that the HUVEC layer was interposed between the dermis tissue layers, compared with the case of performing culture under the condition that the HUVEC and the NHDF were mixed (date not shown).

Example 6

An artificial skin model including lymph capillaries was produced in the same way as in Example 5 except for using lymphatic vessel endothelial cells (LEC) instead of human umbilical vein endothelial cells (HUVEC).

Figures 11A, 11B:
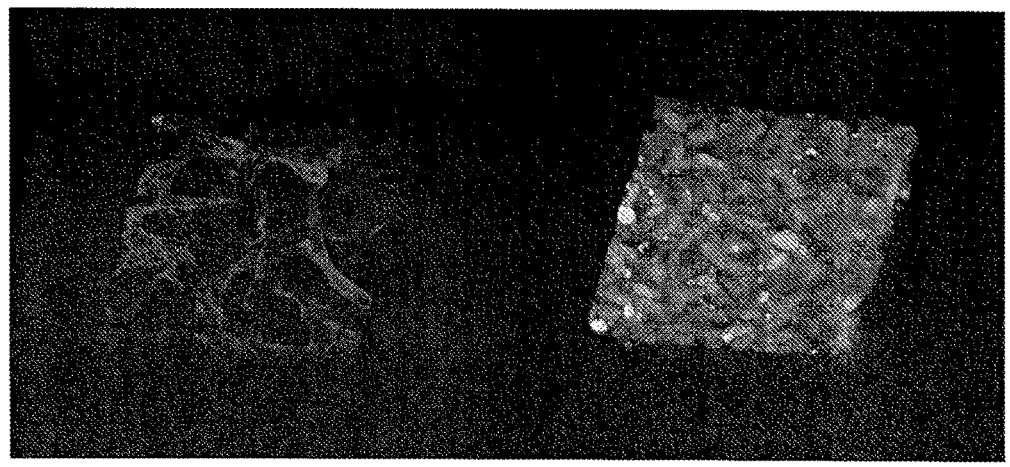
FIG. 11 shows an example of confocal laser scanning microscope (CLSM) images of an artificial skin model of Example 6.

FIG. 11 shows an example of confocal laser scanning microscope (CLSM) images of the obtained artificial skin model. FIG. 11 shows CLSM images of the obtained artificial skin model. FIG. 11A shows an image of the LEC stained in red, and FIG. 11B shows an image of the NHDF stained in green.

In the same way as in Example 5 using the HUVEC, in the case of using the LEC, cells derived from the LEC that had been positioned on the surface of the first dermis tissue layer in the form of pavement stones before the culture also changed to a capillary form by performing culture under the condition that the LEC layer was interposed between the first dermis tissue layer and the second dermis tissue layer. Further, when the culture was performed for further 7 days, lymph capillaries having a tube structure were formed in the artificial skin model as shown in FIG. 11.

The results of Examples 5 and 6 suggested that a novel artificial skin model closer to a skin of a living body, including tissue ancillary organs such as blood capillaries and lymph capillaries, can be provided.

INDUSTRIAL APPLICABILITY

According to the present invention, an artificial skin model can be provided, which allows permeability of a test substance, a minute response involved therein, and the like to be evaluated. Therefore, the present invention is useful, for example, in the fields of cosmetic products, medicine, pharmaceutical production, etc.

The invention claimed is:

1. A production method for producing an artificial skin model, comprising:
   providing cells;
   providing, separately from the cells, a first material having an RGD sequence;
   providing, separately from the cells, a second material which interacts with the first material;
   forming extracellular matrix coated cells;
   forming a dermis tissue layer, in which the extracellular matrix coated cells are laminated, by culturing the extracellular matrix coated cells; and
   forming an epidermis layer by arranging epidermis cells on the dermis tissue layer,
   wherein each of the extracellular matrix coated cells comprises:
      a cell, and
      a coating film coating the cell, wherein the coating film includes the first material and the second material, and at least one of the first material and the second material includes an extracellular matrix component,
   the forming of the extracellular matrix coated cells comprises:
      forming first material coated cells by contacting the first material to the cells by at least one selected from:
      (a) soaking the cells in a liquid containing the first material,
      (b) dripping the liquid containing the first material to the cells, and
      (c) spraying the liquid containing the first material to the cells; and
      then contacting the second material to the first material coated cells by at least one selected from:
      (d) soaking the first material coated cells in a liquid containing the second material,
      (e) dripping the liquid containing the second material to the first material coated cells, and
      (f) spraying the liquid containing the second material to the first material coated cells,
   wherein the first material is fibronectin, and the second material is gelatin.

2. The production method according to claim 1, comprising forming a tissue ancillary organ in the dermis tissue layer.

3. The production method according to claim 1, wherein the forming a dermis tissue layer comprises: forming a cell layer, in which the coated cells are laminated, by culturing the coated cells; arranging cells forming the tissue ancillary organ on the cell layer; and forming a cell layer in which the coated cells are laminated by arranging the coated cells on the cell layer in which the cells forming the tissue ancillary organ are arranged and culturing the coated cells arranged on the cell layer.

4. The production method according to claim 1, wherein the forming a dermis tissue layer comprises arranging the coated cells so that the coated cells are laminated in at least two layers.

5. A production method for producing an artificial skin model, comprising:
   providing cells;
   providing, separately from the cells, a first material having an RGD sequence;
   providing, separately from the cells, a second material which interacts with the first material;
   forming extracellular matrix coated cells;
   forming a dermis tissue layer, in which the extracellular matrix coated cells are laminated, by culturing the extracellular matrix coated cells; and
   forming an epidermis layer by arranging epidermis cells on the dermis tissue layer,
   wherein each of the extracellular matrix coated cells comprises:
      a cell, and
      a coating film coating the cell, wherein the coating film includes the first material and the second material, and at least one of the first material and the second material includes an extracellular matrix component,
   the forming of the extracellular matrix coated cells comprises:
      forming second material coated cells by contacting the second material to the cells by at least one selected from:
      (a) soaking the cells in a liquid containing the second material,
      (b) dripping the liquid containing the second material to the cells, and
      (c) spraying the liquid containing the second material to the cells; and
      then contacting the first material to the second material coated cells by at least one selected from:
      (d) soaking the second material coated cells in a liquid containing the first material,
      (e) dripping the liquid containing the first material to the second material coated cells, and
      (f) spraying the liquid containing the first material to the second material coated cells,
   wherein the first material is fibronectin, and the second material is gelatin.

6. The production method according to claim 5, comprising forming a tissue ancillary organ in the dermis tissue layer.

7. The production method according to claim 5, wherein the forming a dermis tissue layer comprises: forming a cell layer, in which the coated cells are laminated, by culturing the coated cells; arranging cells forming the tissue ancillary organ on the cell layer; and forming a cell layer in which the coated cells are laminated by arranging the coated cells on the cell layer in which the cells forming the tissue ancillary organ are arranged and culturing the coated cells arranged on the cell layer.

8. The production method according to claim 5, wherein the forming a dermis tissue layer comprises arranging the coated cells so that the coated cells are laminated in at least two layers.

* * * * *